United States Patent [19]

Rittersdorf et al.

[11] Patent Number: 5,426,030
[45] Date of Patent: Jun. 20, 1995

[54] APPARATUS FOR DETERMINATION OF HDL CHOLESTEROL

[75] Inventors: Walter Rittersdorf, Mannheim; Ulfert Deneke, Rimbach-Zotzenbach; Gerhard Hiller, Mannheim; Hartmut Merdes, Heidelberg; Klaus Buecker, Viernheim; Uwe Goebbert, Mannheim, all of Germany

[73] Assignee: Boehringer Mannheim GmbH, Mannheim, Germany

[21] Appl. No.: 572,875

[22] Filed: Aug. 24, 1990

[30] Foreign Application Priority Data

Sep. 1, 1989 [DE] Germany .................. 39 29 032.8

[51] Int. Cl.⁶ .................. C12Q 1/60; G01N 21/00; G01N 33/92
[52] U.S. Cl. .................. 435/11; 422/56; 422/57; 436/71; 436/170
[58] Field of Search .................. 435/11, 7.8, 7.1; 436/170, 71; 422/56, 57

[56] References Cited

U.S. PATENT DOCUMENTS 4,414,326  11/1983  Goldberg .................. 435/11
4,477,575  10/1984  Vogel .................. 436/170
4,746,605   5/1988  Kerscher .................. 435/7
4,870,005   9/1989  Ariyoshi .................. 435/7

OTHER PUBLICATIONS

Weber, Walter J. Physicochemical Processed Wiley-Interscience N.Y. 1972 p. 131.
Derwent Abstract 89-061491.
Derwent Abstract 90-295783.
Bachorik et al., Meth. Enzymol 129: 78–100 (2986).

Primary Examiner—William H. Beisner
Assistant Examiner—Ralph Gitomer
Attorney, Agent, or Firm—Felfe & Lynch

[57] ABSTRACT

The invention relates to an apparatus and a method useful in separating non-high density lipoproteins, referred to as "non-HDLs", from biological fluids containing them. A porous carrier is provided which contains a non-HDL precipitating agent. One need only contact the sample of interest to the carrier for one minute or less, after which the precipitated non-HDLs are no longer present in the sample being tested. The applications of the method include the ability to determine high density lipoproteins in the sample without interference from non-HDLs.

8 Claims, 1 Drawing Sheet

APPARATUS FOR DETERMINATION OF HDL CHOLESTEROL

The invention concerns a method for the quantitative determination of HDL (High Density Lipoprotein) in biological fluids and an agent suitable therefor.

Total cholesterol in blood, plasma or serum is one of the best known parameters for assessing the extent of risk of a coronary heart disease.

However, the concentration of total cholesterol is only of limited value for the assessment of individual risk. The measurement of the cholesterol in the lipoproteins of low density (Low Density Lipoproteins=LDL) on the one hand and in the lipoproteins of high density (High Density Lipoproteins=HDL) on the other hand is more meaningful. Epidemiological and clinical studies have shown that there is a positive correlation between LDL cholesterol and coronary heart disease and a negative correlation between HDL cholesterol and coronary heart disease.

As a close approximation the determination of the HDL as well as the total cholesterol is sufficient for an assessment of risk. This course is preferably followed at present in diagnostic practice.

The other lipoprotein classes (LDL, VLDL, chylomicrons) which are present have to be separated in order to determine HDL cholesterol separately. The potential methods of separation are based on differences in the flotation densities (sequential flotation or equilibrium sedimentation, both in the ultracentrifuge), on different surface charges (electrophoreses on paper or agarose as carrier) or on differences in the apolipoproteins (immunochemical methods using specific antibodies). All these methods of separation are expensive, time-consuming and not established in routine laboratories. Precipitation reactions (in Monographs on Atherosclerosis, Vol. 11 (1982), Clackson, T. B., Kritchevsky, D., Pollak, O. J. eds; Lipoprotein Precipitation, Burstein, M., Legmann, P. and in Meth. in Enzymology, Vol. 129 (1986)) whose specificity depends on the particle dimension and the surface charge are cheap, relatively easy to handle and therefore widespread. Polymeric substances serve as precipitation reagents, and these are usually polyanionic. Polymers which are uncharged are also suitable. The polyanions usually need bivalent cations in order to develop their precipitating effect, while the uncharged polymers do not require them.

The experimental procedures and the concentrations which are used for the combined precipitation agents are designed to quantitatively precipitate all lipoproteins except HDL, to separate these precipitates from the liquid fraction of the sample in a suitable manner and subsequently to quantify the HDL in the liquid fraction of the sample by means of a cholesterol assay. For this, depending on how the test is carried out, a defined volume of precipitating agent (in suitable concentrations) is mixed intensively with a defined volume of the sample to be determined. It is the state of the art to allow a reaction time of at least 10 minutes for the precipitation and only after this time interval has elapsed to separate sedimented non-HDL lipoprotein precipitates and HDL remaining in the liquid fraction by centrifugation. The centrifugation step also needs some time.

This method is much too time-consuming for a routine test. In addition, centrifugation steps with subsequent separation of the supernatant need complicated additional equipment and a transfer step. The required pipetting procedure in which a defined amount of supernatant is taken is, in addition, a source of error which can lead to less precise measurements.

It is therefore the object of the invention to avoid the disadvantages of the state of the art and to provide a method for the separation of non-HDL lipoproteins from biological fluids, which can be carried out more rapidly and without complicated additional equipment and which allows a more rapid and a simpler HDL cholesterol determination.

The object is achieved by a method for the separation of non-HDL lipoproteins from biological fluids, in which the biological fluid containing non-HDL lipoproteins is applied onto a carrier through which liquids can flow and which contains a precipitating agent for non-HDL lipoproteins. The invention also provides an agent for the separation of non-HDL lipoproteins and a rapid diagnostic agent which contains this agent.

Figure 1:
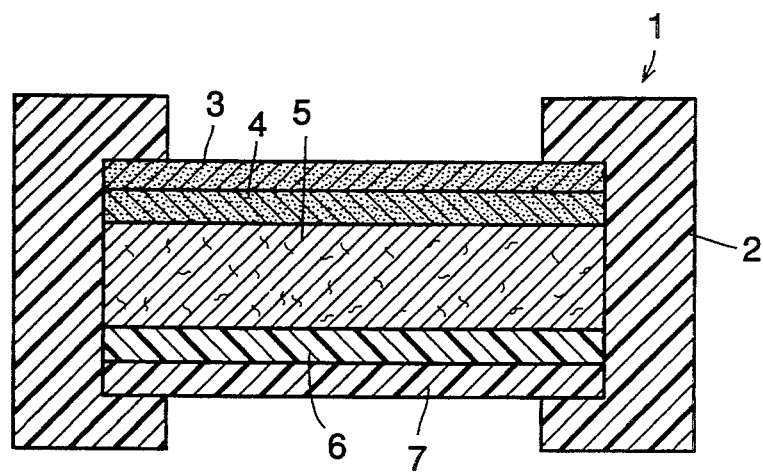
FIG. 1 represents a cross-section showing the layers of the test strip.

It has been found that the precipitation of the non-HDL lipoproteins proceeds particularly rapidly and specifically with conventional, well-known precipitating agents when these precipitating agents are applied in a finely dispersed form onto a carrier through which liquids can flow and the sample has to flow through this carrier. In general, the precipitation takes less than 1 minute. Carriers through which liquids can flow are: papers, fabrics made of synthetic fibres such as polyester or polyamide or others, fabrics made of natural fibres such as cotton, silk or others or mixtures of these materials. In this connection, the structure of the fabrics can be monofilament or multifilament, multifilament forms being preferred.

The fibres which compose the carrier through which liquids can flow preferably have a fibre diameter from 3 to 100 $\mu$m, preferably 5 to 50 $\mu$m. The carrier has, in particular, a weight per unit area of 10 to 100 g/m$^2$, preferably 10 to 50 g/m$^2$ at a thickness of 0.030 to 0.150 mm, and the ability to absorb water is 25 to 100 g/m$^2$, preferably 40 to 70 g/m$^2$ at the thicknesses mentioned above.

Other suitable carriers are arrangements of glass fibres and mixtures of glass fibres with the fibres mentioned above through which liquids can flow—preferably in the form of fleeces—and membranes in different forms. The membranes should have hydrophilic properties, a thickness between 20–250 $\mu$m, preferably 70–150 $\mu$m and pore sizes between 0.2–20 $\mu$m, preferably 5–15 $\mu$m.

The transport of liquid in these carriers is based on capillary forces.

The precipitating agents are preferably applied to the carrier by impregnating the carrier with a solution, emulsion or suspension of the precipitating agent and subsequent drying. In this process other useful additives such as pH buffer substances or detergents etc. can also be applied.

In this construction all chemical compounds are suitable as precipitating agents which can also be used in a "wet chemical" process for the precipitation of lipoproteins as long as they dissolve quickly enough in the sample solution. Certain polyanions in combination with bivalent cations are particularly well known. Examples of these include combinations of phosphotungstic acid and magnesium chloride, of heparin and manganese (II) chloride or of dextran sulphate and magnesium chloride. It should be noted that, in principle, each polyanion can be combined with each of the three cations ($Mg^{2+}$, or $Mn^{2+}$, or $Ca^{2+}$) which results, however, in slight differences in their capacity to precipitate lipoproteins (Burstein, 1986). The concentration of the chosen cation can be adapted accordingly in order to specifically precipitate the non-HDL lipoproteins. The molecular size of the polyanion used also influences the capacity to precipitate lipoproteins and should be taken into account when choosing the concentrations. The use of dextran sulphate with a molecular weight of 500000 and 50000, for example, is known. Both are also suitable for an application on carriers through which liquids can flow. Dextran sulphate with a molecular weight of 50000 combined with $Mg^{2+}$ is, however, preferred in which case $Mg^{2+}$ is preferably used in the form of magnesium acetate. In principle, magnesium sulphate, magnesium chloride and magnesium aspartate can also be used.

The concentration of the precipitating agent can be matched exactly to the volume of the sample to be examined.

The non-HDL lipoproteins are precipitated by bringing a sample into contact with the carrier through which liquids can flow and which contains the precipitating agent. The precipitation reaction is started thereby. The time interval during which the sample is in contact with the precipitating agent on the precipitating agent carrier can be adjusted in a simple manner by varying the suction pressure by means of the interstitial volumes or the hydrophilicity of the carrier. The achieved flow rates of the sample through the carrier are very important for the test performance. The precipitate formation is completed after less than one minute, at best even after about 10 second and the liquid can be removed from the carrier material. This can be effected continously or discontinously, for example by decanting, using gravitational force or by aspirating. The fluid is preferably drawn into a further carrier by capillary forces in which the precipitated non-HDL lipoproteins are separated. This process requires that the carriers are in contact with one another. The separation of the precipitates by other methods such as centrifugation is less preferable even though this is also possible without losing the advantage of the fast precipitation.

It was found that lipoprotein precipitates which are formed by the action of a combination of polyanions and the bivalent cations mentioned above on biological samples can be retained in a mesh of fibres.

The arrangement of the fibres in the mesh is preferably disordered. Glass fibres, cellulose fibres, polyamide fibres and polyester fibres or mixtures thereof are preferably used as the fibres. Glass fibres and mixtures with the fibres mentioned above are particularly preferred. The fibres which make up the mesh preferably have a diameter of 0.2 to 10.0 $\mu$m, preferably a diameter of 0.5 to 5.0 $\mu$m. The mesh has a weight per unit area of 20 to 50 g/m², preferably 23 to 30 g/m² and a capacity to absorb water of 250 to 500 g/m², preferably of 320 to 420 g/m² thickness of 0.19 to 0.23 mm.

Systems containing glass fibres, their possible spatial arrangement and the dimension of the fibres are described in detail in DE 30 29 579. Furthermore, the mesh of fibres can be hardened by the addition of suitable binding agents, either of an inorganic nature (e.g. water glass) or organic nature (e.g. polymers such as polyvinyl acetate, polyacrylic acid ester or similar polymers). These additives inter alia agglutinate the fibres at those positions where they are in contact with one another and in this way they improve the mechanical stability of the fibre mesh.

The liquid fraction of the applied sample spreads unhindered through the whole mesh and it can also leave it when the geometric arrangement is approximately arranged or configured or by overcoming the internal capillary forces of the membrane. In this way the separation of precipitated non-HDL lipoproteins and non-precipitated HDL can be achieved with simple devices. Biological fluids from which the non-HDL lipoproteins can be separated according to the present invention include whole blood, serum and plasma.

The method can be particularly advantageously used in methods for the quantitative determination of HDL cholesterol on test strips. For this, the fluid from which the non-HDL lipoproteins have been separated according to the method described above, is brought into contact with reagents which are necessary and/or useful for carrying out the test reaction, for example a test reaction for cholesterol. Such reagents are known to the expert, for example from EP-B-0016387, and can be adapted to the expected cholesterol concentrations (0–100 mg/dl). They can for example, also be present in the form of a film or a coating on a porous carrier. Such embodiments of reagent forms are known to the man skilled in the art.

An embodiment of a method for the determination of HDL cholesterol which contains the preferred embodiment for separating the non-HDL lipoproteins is shown in FIG. 1. A rapid diagnostic agent (1) contains several layers of a carrier in a casing (2).

A fibre mesh (5) with a separating capacity for lipoprotein precipitates which is adjusted to the chosen sample volume is underneath a carrier through which liquids can flow and which is impregnated with a precipitating agent (4). Adjoining this is a suitable absorptive cholesterol determining test film (6) which is capable of taking up fluid free of precipitate from the fibre mesh. The test film is coated on a transparent foil (7). The determination is started by applying the sample liquid over the carrier containing the precipitating agent. The measurement signal which develops can be evaluated visually or photometrically from the foil side of the construction.

This simple design is not well-suited for the investigation of whole blood. If whole blood is to be used, then the cellular blood components are preferably separated in a layer (3) in front of the carrier for the precipitating agent e.g. by agents which are described in detail in DE-A-30 29 579.

Figure 2:
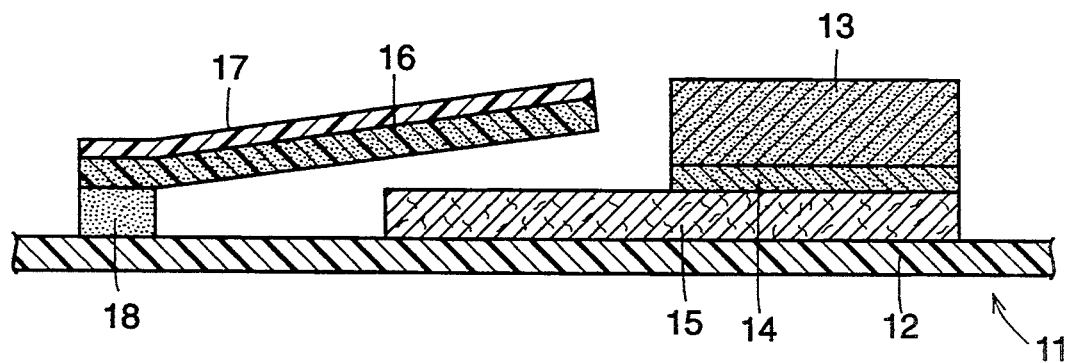
FIG. 2 represents a side view of the test strip.

With regard to the well-known temperature dependency of enzymatic reactions, the geometric arrangement of the test design can also be so chosen that the cholesterol test is separated by time from the previous reaction steps. This also allows a controlled regulation of the temperature of the test step. A corresponding test construction is outlined in DE-A-3130749. The preferred construction of a rapid diagnostic agent for HDL in a test strip form (11) is shown in FIG. 2. A fibre mesh (15), a carrier through which liquids can flow and which contains a precipitating agent (14) as well as a separating layer for cellular components (13) are mounted on top of one another on a supporting foil (12). The fibre mesh (15) protrudes from under the carriers (13) and (14) towards a flap. The flap, which consists of a transparent foil (17) and a test film for cholesterol (16) is attached to the supporting foil (12) via an adhesive join (18).

The sample to be investigated is applied to the layer (13) and flows through the layers (14) and (15), during which the non-HDL lipoproteins are separated, into the mesh (15) under the flap. The test reaction is started by pressing the flap with the test layer (16) onto the layer (15). The change in colour can be followed by means of a photometer or a reflection photometer.

In this case in comparison with the embodiment outlined in FIG. 1 lateral separating capacity of the fibre mesh is also effective.

The method according to the present invention has other major advantages over the known methods. It is possible to use particularly small liquid volumes. The handling of the device according to the present invention is very simple. Only two basic handling steps are necessary, namely the application of a liquid sample and the reading of a measurement after a particular time. Other instruments are not needed apart from a suitable photometer in the case of a quantitative determination. Transfer steps are not needed. All types of blood, even whole blood, can be easily used when a separating pad for cells is used first. If anticoagulants have been added to the sample to be examined, it is recommended that their effects on the determination be compensated. The separation of non-HDL lipoproteins can be carried out in less than 60 seconds. The dosage of the sample volume is greatly simplified.

Examples for the invention are given in the following:

EXAMPLE 1

Precipitating agent carrier (14 or 4) for EDTA plasma

A multifilament polyester fabric (100 μm mesh size, 105 μm fabric thickness, 55 threads per cm, with 815 ul water passage per $m^2$ and sec) is impregnated with a solution of the following composition:

| Hepes buffer, 50 mM; pH 7.0 | 78.00 g |
|---|---|
| magnesium acetate × $4H_2O$ | 15.68 g |
| dextran sulphate (MW 50000) | 2.57 g |
| bovine serum albumin | 1.78 g |

A coating of about 57 ml/$m^2$ is obtained.

After drying under a flow of warm air the impregnated fabric is cut into suitable unit areas which match the corresponding test procedure and they are integrated into the test construction.

EXAMPLE 2

Precipitating agent carrier (14 or 4) for serum

The following impregnating solution is used in a procedure analogously to Example 1:

| Hepes buffer, 50 mM; pH 7.0 | 78.00 g |
|---|---|
| magnesium acetate × $4H_2O$ | 10.10 g |
| dextran sulphate (MW 50000) | 2.57 g |
| bovine serum albmin | 1.78 g |
| $H_2O$ | 5.58 g |

EXAMPLE 3

Precipitating agent carrier (14 or 4) for blood

A paper of suitable thickness and absorptivity e.g. tea bag paper with a weight per unit area of 12 g/$cm^2$ and a thickness of 50 μm is impregnated with the following impregnating solution:

| Hepes buffer, 50 mM; pH 7.0 | 70.20 g |
|---|---|
| magnesium acetate × $4H_2O$ | 4.78 g |
| dextran sulphate (MW 50000) | 2.54 g |
| bovine serum albumin | 1.60 g |
| $H_2O$ | 7.80 g |

A coating of about 63 ml/$m^2$ is obtained with this carrier.

EXAMPLE 4

Test film

A dispersion of the following composition:

| K/Na phosphate buffer, 0.5 M; pH 7.0 | 17.14 g |
|---|---|
| Keltrol F | 0.19 g |
| $TiO_2$ (powder) | 1.31 g |
| dioctyl sodium sulphosuccinate | 0.40 g |
| polyvinylpropionate dispersion (50% in $H_2O$) | 11.70 g |
| diatomaceous earth (Celatom MW 25) | 17.65 g |
| phenylsemicarbazide | 0.025 g |
| 2(4-hydroxy-3,5-dimethoxyphenyl)-4-(4-dimethyl-aminophenyl)-5-methyl-imidazole-dihydrochloride | 0.061 g |
| methanol | 1.74 g |
| $H_2O$ | 46.28 g |
| cholesterol esterase | 23700 U |
| cholesterol oxidase | 6500 U |
| peroxidase | 230000 U |
| hexanol | 2.07 g | is prepared for the production of a reagent film in order to quantify HDL cholesterol.

The dispersion is applied as a layer of 300 μm thickness onto a polycarbonate foil and dried with warm air. The reagent coating which results forms a graded blue colouration with fluids containing cholesterol depending on the cholesterol content.

| cholesterol concentration | remission R % (measurements in the reflection photometer Reflotron$^R$) |
|---|---|
| 0 | 70.0 |
| 20 | 43.0 |
| 40 | 29.0 |
| 60 | 22.0 |
| 80 | 18.5 |
| 100 | 16.0 |

EXAMPLE 5

Fibre mesh

A mixture of borosilicate glass fibres with a fibre diameter of ca. 0.6 μm and cellulose fibres with a fibre diameter of ca. 4 μm, preferably in the ratio of 9:1. was used the mixture has a weight per unit area ca. 25 g/$m^2$ at a mesh thickness of ca. 0.21 mm; the ability of the mesh to take up water of about 370 g/$m^2$.

EXAMPLE 6

Production of a rapid diagnostic agent (11) for the determination of HDL

If the test construction of FIG. 2 is chosen, the following measurements apply for the different layers:

12: 100×6 mm
13: 5×6 mm (borosilicate fleece according to DE-A-3029579, weight per unit area ca. 60 g/m²)
14: 6×6 mm
15: 16×6 mm
16/17: 15×6 mm This embodiment is suitable for a sample volume between 28–32 μl and is particularly advantageous.

It will be understood that the specification and examples are illustrative but not limitative of the present invention and that other embodiments within the spirit and scope of the invention will suggest themselves to those skilled in the art.

We claim:

1. Apparatus for determining high density lipoprotein (HDL) cholesterol in a lipoprotein containing body fluid sample, comprising:
   (i) a sample application layer,
   (ii) a porous carrier layer containing a precipitating agent which precipitates non high density lipoproteins (non HDLs) but not HDL, wherein said porous carrier layer is in fluid contact with said sample application layer,
   (iii) a fluid transport means, a first portion of which is in fluid contact with said porous carrier layer, a second portion of which extends away from said porous carrier layer,
   (iv) a support means attached to said fluid transport means, and
   (v) a reagent layer which contains a cholesterol determining reagent, wherein said reagent layer is attached to said support means by a connecting means which permits contact of said reagent layer to said second portion of said fluid transport means upon application of pressure to said reagent layer.

2. The apparatus of claim 1, wherein said porous carrier layer comprises a fiber fleece having a weight per unit area of from 10 to 100 g/m² and a water absorbing capacity of 25 to 200 g/m² at a thickness of from 0.030 to 0.150 mm.

3. The apparatus of claim 2, wherein said fleece comprises fibers having a diameter of from 3 to 100 um.

4. The apparatus of claim 2, wherein the fibers of said fiber fleece comprise synthetic resin fibers, natural fibers or glass fibers.

5. The apparatus of claim 1, wherein said precipitating agent comprises a combination of (i) a polyanion selected from the group consisting of phosphotungstic acid, heparin and dextran sulphate, and (ii) a bivalent cation selected from the group consisting of $Mg^{2+}$, $Mn^{2+}$, and $Ca^{2+}$.

6. The apparatus of claim 5, wherein said polyanion is dextran sulphate having a molecular weight of about 50,000 g/mol, and said bivalent cation is $Mg^{2+}$, in the form of magnesium acetate.

7. The apparatus of claim 1, wherein said porous carrier layer comprises a hydrophilic membrane having a thickness of from 20–250 um and a pore size of from 0.2 to 20 um.

8. Apparatus for determining high density lipoprotein (HDL) cholesterol in a lipoprotein containing body fluid sample, comprising: (i) a sample application layer,
   (ii) a first porous carrier layer containing a precipitating agent which precipitates non high density lipoproteins (non HDLs) but not HDL, wherein said porous carrier layer is in fluid contact with said sample application layer,
   (iii) a second porous carrier layer comprising a fiber mesh, the fibers of which have a weight per unit area of from 20 to 50 g/cm², and water absorbing capacity of 250–500 g/m² at a thickness of from 0.19 to 0.23 mm,
   (iv) a fluid transport means, a first portion of which is in fluid contact with said porous carrier layer, a second portion of which extends away from said porous carrier layer,
   (v) a support means attached to said fluid transport means, and
   (vi) a reagent layer which contains a cholesterol determining reagent, wherein said reagent layer is attached to said support means by a connecting means which permit contact of said reagent layer to said second portion of said fluid transport means upon application of pressure to said reagent layer.

* * * * *